US010335768B2

(12) United States Patent
Ahn et al.

(10) Patent No.: US 10,335,768 B2
(45) Date of Patent: Jul. 2, 2019

(54) SUPER ABSORBENT POLYMER

(71) Applicant: LG Chem, Ltd., Seoul (KR)

(72) Inventors: Tae Bin Ahn, Daejeon (KR); Chang Sun Han, Daejeon (KR); Seung Do Hong, Daejeon (KR); Chul Hee Ryu, Daejeon (KR); Dong Hyun Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/531,940

(22) PCT Filed: Mar. 30, 2016

(86) PCT No.: PCT/KR2016/003262
§ 371 (c)(1),
(2) Date: May 31, 2017

(87) PCT Pub. No.: WO2017/164452
PCT Pub. Date: Sep. 28, 2017

(65) Prior Publication Data
US 2018/0185819 A1 Jul. 5, 2018

(30) Foreign Application Priority Data
Mar. 23, 2016 (KR) .................. 10-2016-0034589

(51) Int. Cl.
*B01J 20/26* (2006.01)
*B01J 20/28* (2006.01)

(52) U.S. Cl.
CPC ....... *B01J 20/267* (2013.01); *B01J 20/28004* (2013.01); *B01J 20/28016* (2013.01)

(58) Field of Classification Search
None
See application file for complete search history.

(56) References Cited

U.S. PATENT DOCUMENTS

| 5,562,646 A | 10/1996 | Goldman et al. |
| 9,701,796 B2 * | 7/2017 | Jung ................. A61L 15/60 |
| 2007/0207924 A1 | 9/2007 | Ikeuchi et al. |
| 2013/0026412 A1 * | 1/2013 | Machida ............. C08F 6/008 252/194 |
| 2013/0210947 A1 | 8/2013 | Weismantel et al. |

(Continued)

FOREIGN PATENT DOCUMENTS

| EP | 2518092 A1 | 10/2012 |
| EP | 2535027 A1 | 12/2012 |

(Continued)

OTHER PUBLICATIONS

International Search Report and Written Opinion for Application No. PCT/KR2016/003262, dated Dec. 20, 2016.

(Continued)

*Primary Examiner* — Joseph D Anthony
(74) *Attorney, Agent, or Firm* — Lerner, David, Littenberg, Krumholz & Mentlik, LLP

(57) ABSTRACT

The present invention relates to a super absorbent polymer which is excellent in various physical properties required for a super absorbent polymer, while exhibiting excellent water absorption capacity, absorption rate and liquid permeability, and a method for preparing the same.

4 Claims, 1 Drawing Sheet

(56) References Cited

U.S. PATENT DOCUMENTS

| | | | | |
|---|---|---|---|---|
| 2014/0312273 | A1* | 10/2014 | Wattebled | C08J 3/245 |
| | | | | 252/194 |
| 2015/0080821 | A1 | 3/2015 | Peri et al. | |
| 2015/0080822 | A1 | 3/2015 | Ehmsperger et al. | |
| 2015/0299404 | A1* | 10/2015 | Daniel | C08F 220/06 |
| | | | | 604/365 |
| 2015/0376318 | A1 | 12/2015 | Haag et al. | |
| 2016/0096944 | A1 | 4/2016 | Wattebled et al. | |
| 2016/0311985 | A1* | 10/2016 | Jung | A61L 15/60 |
| 2016/0332141 | A1 | 11/2016 | Machida et al. | |
| 2016/0375171 | A1* | 12/2016 | Omori | A61L 15/26 |
| | | | | 525/329.7 |
| 2017/0065739 | A1 | 3/2017 | Braun et al. | |

FOREIGN PATENT DOCUMENTS

| | | |
|---|---|---|
| EP | 2557095 A1 | 2/2013 |
| EP | 3067370 A1 | 9/2016 |
| JP | 3415036 B2 | 6/2003 |
| JP | 2009531158 A | 9/2009 |
| JP | 4866733 B2 | 2/2012 |
| KR | 20130093477 A | 8/2013 |
| KR | 20150067729 A | 6/2015 |
| WO | 2007116777 A1 | 10/2007 |
| WO | 2011126079 A1 | 10/2011 |
| WO | 2014183987 A1 | 11/2014 |
| WO | 2015041784 A1 | 3/2015 |
| WO | 2015088200 A1 | 6/2015 |
| WO | 2015169912 A1 | 11/2015 |
| WO | 2015175620 A1 | 11/2015 |

OTHER PUBLICATIONS

Odian, George, "Principles of Polymerization," Second Edition, Oct. 1981, p. 203, John Wiley & Sons, Inc.

Schwalm, Reinhold, "UV Coatings Basics, Recent Developments and New Applications," Dec. 21, 2006, pp. 113-115, ISBN-10: 0444529799. ISBN-13: 978-0444529794.

Third Party Observation for Application No. EP16863189.3 dated Aug. 9, 2018.

Third Party Observation for Application No. PCT/KR2016/003262 dated Jul. 23, 2018.

\* cited by examiner

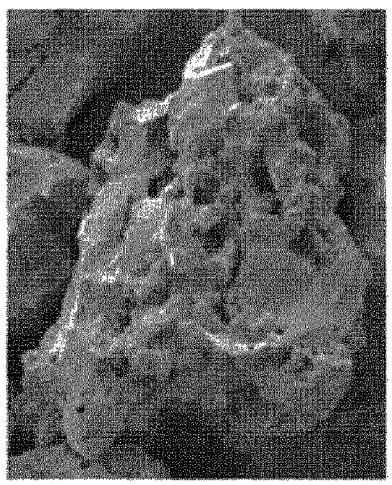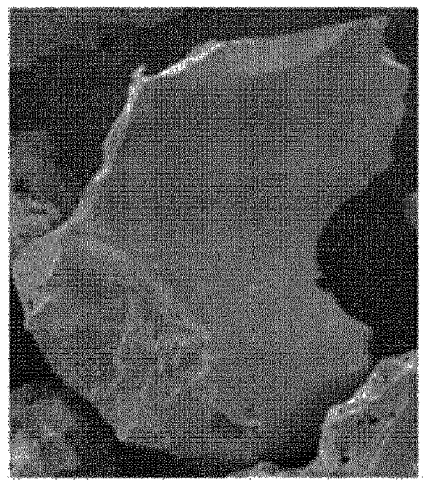

SUPER ABSORBENT POLYMER

CROSS-REFERENCE TO RELATED APPLICATION(S)

The present application is a national phase entry under 35 U.S.C. § 371 of International Application No. PCT/KR2016/003262, filed Mar. 30, 2016, published in Korean, which claims priority to and the benefit of Korean Patent Application No. 10-2016-0034589, filed on Mar. 23, 2016 with the Korean Intellectual Property Office, the disclosures of which are incorporated herein by reference in their entirety.

TECHNICAL FIELD

The present invention relates to a super absorbent polymer which is excellent in various physical properties required for a super absorbent polymer, while exhibiting excellent water absorption capacity, absorption rate and liquid permeability, and a method for preparing the same.

BACKGROUND OF ART

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for preparation of various products, for example, hygiene products such as paper diapers for children, water retaining soil products for gardening, water stop materials for the civil engineering and construction, sheets for raising seedling, fresh-keeping agents for food distribution fields, materials for poultice or the like.

In most cases, these super absorbent polymers have been widely used in the field of hygienic materials such as diapers or sanitary napkins. For these applications, the super absorbent polymer should exhibit a high moisture absorbency, it should not release the absorbed water even in the external pressure, and additionally it should well retain the shape even in a state where the volume is expanded (swelled) by absorbing water, and thereby exhibit excellent liquid permeability.

In recent years, as the demand for a thin diaper increases, the proportion of the absorbent polymer in the diaper tends to increase. Therefore, the water absorbent polymer needs to have the performance of the fiber material of the diaper. For this, the water absorbent polymer should have a high water absorption capacity as well as a high absorption rate and a liquid permeability.

In the process of producing the water absorbent polymer, it is generally necessary to pulverize the hydrogel prepared by polymerizing the monomer of the water absorbent polymer. The pulverization of the hydrogel is a process required for producing a super absorbent polymer in the form of a powder or a particle, and this process greatly affects the physical properties of the super absorbent polymer.

In this regard, various studies have been undertaken. As an example, Japanese Patent No. 3415036 discloses a preparation method that minimizes damage to hydrogel during pulverization of the hydrogel, in order to reduce a water-soluble component that can induce a reduction in water absorption capacity. However, the above method can achieve a high water absorption capacity, but it is insufficient to obtain the absorption rate at the level recently required for diapers.

As another example, Japanese Patent No. 4866733 discloses a method of using an internal-crosslinking agent in an amount of 0.2 mol % or more and adjusting the perforation diameter of the perforated plate of the screw type extruder during pulverization of the hydrogel, in order to improve the liquid permeability and absorption rate of the super absorbent polymer. However, the method disclosed herein can achieve a high absorption rate and a liquid permeability, but there is a problem that the water absorption capacity is lowered.

For these reasons, there is a continuing need to develop a technique capable of providing a super absorbent polymer having improved water absorption capacity, absorption rate and liquid permeability while maintaining excellent basic absorption performance.

DETAILED DESCRIPTION OF THE INVENTION

Technical Problem

For resolving the aforesaid problems of the prior arts, it is an object of the present invention to provide a super absorbent polymer which is excellent in various physical properties required for a super absorbent polymer, while exhibiting excellent water absorption capacity, absorption rate and liquid permeability.

It is another object of the present invention to provide a method for preparing the above-mentioned super absorbent polymer.

Technical Solution

In order to achieve these objects, the present invention provides a super absorbent polymer comprising:

a base polymer powder containing a first crosslinked polymer of a water-soluble ethylene-based unsaturated monomer having an acidic group in which at least a part thereof is neutralized; and a surface-crosslinked layer containing a second crosslinked polymer formed on the base polymer powder in which the first crosslinked polymer is additionally crosslinked via a surface crosslinking agent, wherein the super absorbent polymer has:

a centrifuge retention capacity (CRC) for a physiological saline solution (0.9 wt % aqueous sodium chloride solution) for 30 minutes, of 25 g/g or more, an absorbency under pressure (AUP) for a physiological saline solution (0.9 wt % aqueous sodium chloride solution) under 0.7 psi for 1 hour, of 21 g/g or more, a saline flow conductivity (SFC) for a physiological saline solution (0.685 wt % aqueous sodium chloride solution), of 30 ($\cdot{-}7$ cm$^3$·s/g) or more, and T-20 indicating the time required for absorbing 1 g of the super absorbent polymer to 20 g of 0.9 wt % sodium chloride and 0.01 wt % aqueous solution of alcohol ethoxylate having 12 to 14 carbon atoms, of 190 seconds or less.

The present inventors have conducted intensive studies for preparing a super absorbent polymer which is excellent in various physical properties required for a super absorbent polymer, while exhibiting excellent water absorption capacity, absorption rate and liquid permeability. As a result, the inventors have found that the pulverization condition of the hydrogel as described below affects the above-described physical properties. Thus, by adjusting the pulverization condition of the hydrogel, a super absorbent polymer having high water absorption capacity, absorption rate and liquid permeability, which could not be achieved conventionally, has been prepared. Furthermore, it was found that various physical properties required for the super absorbent polymer are excellent in addition to the above physical properties.

Hereinafter, the present invention will be described in detail.

As used herein, the term "super absorbent polymer" means a super absorbent polymer comprising: a base polymer powder containing a first crosslinked polymer of a water-soluble ethylene-based unsaturated monomer having an acidic group in which at least a part thereof is neutralized; and a surface-crosslinked layer containing a second crosslinked polymer formed on the base polymer powder in which the first crosslinked polymer is additionally crosslinked via a surface crosslinking agent.

The water-soluble ethylene-based unsaturated monomer may be any monomer conventionally used in the production of a super absorbent polymer. As a non-limiting example, the water-soluble ethylene-based unsaturated monomer may be a compound represented by the following Chemical Formula 1:

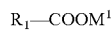  [Chemical Formula 1]

in Chemical Formula 1, $R_1$ is an alkyl group having 2 to 5 carbon atoms containing an unsaturated bond, and $M^1$ is a hydrogen atom, a monovalent or divalent metal, an ammonium group, or an organic amine salt.

Preferably, the monomer may be at least one selected from the group consisting of acrylic acid, methacrylic acid, and monovalent metal salts, divalent metal salts, ammonium salts, and organic amine salts of these acids. When an acrylic acid or a salt thereof is used as the water-soluble ethylene-based unsaturated monomer, it is advantageous because a super absorbent polymer having improved water absorptivity can be obtained. In addition, the above-mentioned monomer used herein may include at least one selected from the group consisting of an anionic monomer such as maleic anhydride, fumaric acid, crotonic acid, itaconic acid, 2-acryloyl ethane sulfonic acid, 2-methacryloyl ethane sulfonic acid, 2-(meth)acryloyl propane sulfonic acid, or 2-(meth)acrylamide-2-methylpropane sulfonic acid, and a salt thereof; a nonionic hydrophilic monomer such as (meth)acrylamide, N-substituted (meth)acrylate, 2-hydroxyethyl (meth)acrylate, 2-hydroxypropyl(meth)acrylate, methoxypolyethyleneglycol(meth)acrylate, or polyethyleneglycol (meth)acrylate; and an unsaturated monomer containing amino group such as (N,N)-dimethylaminoethyl(meth)acrylate or (N,N)-dimethylaminopropyl(meth)acrylamide, and a quaternary compound thereof.

Here, the water-soluble ethylene-based unsaturated monomer may have an acidic group, in which at least a part of the acidic group is neutralized. Preferably, those in which the monomer is partially neutralized with an alkaline substance such as sodium hydroxide, potassium hydroxide, ammonium hydroxide or the like can be used.

At this time, the degree of neutralization of the monomer may be 40 to 95 mol %, or 40 to 80 mol %, or 45 to 75 mol %. The range of the degree of neutralization may vary depending on the final physical properties. An excessively high degree of neutralization causes the neutralized monomers to be precipitated, and thus polymerization may not readily occur, whereas an excessively low degree of neutralization not only deteriorates the absorbency of the polymer but also endows the polymer with hard-to-handle properties, like elastic rubber.

The "first crosslinked polymer" means that the above-mentioned water-soluble ethylene-based unsaturated monomer is polymerized, and the "base polymer powder" means a substance containing such a first crosslinked polymer. In addition, the "second crosslinked polymer" means a substance in which the first crosslinked polymer is additionally crosslinked via a surface crosslinking agent, whereby the second crosslinked polymer is formed on the base polymer powder. The surface crosslinking agent will be described later.

The super absorbent polymer according to the present invention is excellent in water absorption capacity, absorption rate and liquid permeability, which can be expressed by physical properties such as CRC, AUP, SFC, T-20 and FSR.

Specifically, the super absorbent polymer according to the present invention has a centrifuge retention capacity (CRC) for a physiological saline solution (0.9 wt % aqueous sodium chloride solution) for 30 minutes of 25 g/g or more, preferably 25.5 g/g or more, or 26 g/g or more. Higher the value of CRC, the more excellent it is. Thus, the upper limit thereof is not limited, but as an example, it is 37 g/g or less, 36 g/g or less, 35 g/g or less, or 34 g/g or less. The centrifuge retention capacity (CRC) for a physiological saline can be calculated by the following Equation 1 after absorbing the super absorbent polymer in a physiological saline solution over 30 minutes:

$$CRC(g/g) = \{[W_2(g) - W_1(g) - W_0(g)]/W_0(g)\} \quad \text{[Equation 1]}$$

in Equation 1, $W_0(g)$ is an initial weight(g) of the super absorbent polymer, $W_1(g)$ is a weight of bag measured after impregnating a nonwoven fabric bag not containing a super absorbent polymer in a physiological saline solution at room temperature for 30 minutes and then dehydrating the same by using a centrifuge at 250 G for 3 minutes, and $W_2(g)$ is a weight of bag measured after impregnating a nonwoven fabric bag containing a super absorbent polymer in physiological saline at room temperature for 30 minutes and then dehydrating the same by using a centrifuge at 250 G for 3 minutes.

In addition, the super absorbent polymer according to the present invention has an absorbency under pressure (AUP) for a physiological saline solution (0.9 wt % aqueous sodium chloride solution) under 0.7 psi for 1 hour of 21 g/g or more, preferably 22 g/g or more, or 23 g/g or more. The higher the value of AUP, the more excellent it is. Thus, the upper limit thereof is not limited, and as an example, it is 30 g/g or less, 29 g/g or less, or 28 g/g or less. The AUP can be calculated according to the following Equation 2 after absorbing the super absorbent polymer in a physiological saline solution under a pressure of 0.7 psi over a period of 1 hour:

$$AUP(g/g) = [W_4(g) - W_3(g)]/W_0(g) \quad \text{[Equation 2]}$$

in Equation 2, $W_0(g)$ is an initial weight (g) of the super absorbent polymer, $W_3(g)$ is the total sum of a weight of the super absorbent polymer and a weight of the device capable of providing a load to the super absorbent polymer, and $W_4(g)$ is the total sum of a weight of the super absorbent polymer and a weight of the device capable of providing a load to the super absorbent polymer, after absorbing a physiological saline solution to the super absorbent polymer under a load (0.7 psi) for 1 hour.

In addition, the super absorbent polymer according to the present invention has a saline flow conductivity (SFC, $10^{-7}$ cm$^3$·s/g) for a physiological saline solution (0.685 wt % aqueous sodium chloride solution) of 30 or more, preferably 40 or more, 50 or more, 60 or more, 70 or more, 80 or more, 85 or more, or 90 or more. The higher the value of SFC, the more excellent it is. Thus, the upper limit thereof is not limited, but as an example, it is 190 or less, 180 or less, 170 or less, 160 or less, 150 or less, 140 or less, or 130 or less. The saline flow conductivity (SFC) may be measured and calculated according to methods well known to those skilled in the art, for example, the methods disclosed in columns 54 to 59 of U.S. Pat. No. 5,562,646.

Further, the super absorbent polymer according to the present invention has T-20 of 190 seconds or less which indicates the time required for absorbing 1 g of the super absorbent polymer to 20 g of aqueous solution of sodium chloride and alcohol ethoxylate having 12 to 14 carbon atoms. The smaller the value of T-20 is, the more excellent it is. Thus, the lower limit thereof is not limited, but as an example, it is 80 seconds or more, 90 seconds or more, or 100 seconds or more. 9 g of sodium chloride (0.9 wt %) and 0.1 g of Lorodac (main component: linear alcohol ethoxylate having 12 to 14 carbon atoms, CAS #68439-50-9) (0.01 wt %) are dissolved in 1 L of distilled water to make an aqueous solution, and the T-20 can be calculated and measured with the time required for absorbing 1 g of the super absorbent polymer to 20 g of this aqueous solution. Specific measurement methods of T-20 are described in detail on pages 13 to 18 of European Patent Publication No. 2,535,027.

Further, the super absorbent polymer according to the present invention has the free swell rate (FSR) of 0.20 g/g/s or more, preferably 0.22 g/g/s or more, 0.24 g/g/s or more, or 0.26 g/g/s or more, when 1 g of the super absorbent polymer absorbs 20 g of a 0.9 wt % aqueous sodium chloride solution. The higher the value of FSR is, the more excellent it is. Thus, the upper limit thereof is not limited, but as an example, it is 0.40 g/g/s or less, 0.39 g/g/s or less, 0.38 g/g/s or less, 0.37 g/g/s or less, or 0.36 g/g/s or less.

In addition, the present invention provides a method for preparing a super absorbent polymer comprising the steps of:
1) crosslinking a water-soluble ethylene-based unsaturated monomer having an acidic group in which at least a part thereof is neutralized, in the presence of an internal crosslinking agent, to prepare a hydrogel polymer containing a first crosslinked polymer;
2) pulverizing the hydrogel polymer;
3) drying the pulverized hydrogel polymer;
4) pulverizing the dried polymer; and
5) performing surface modification of the pulverized polymer,
wherein the pulverization of the hydrogel polymer is carried out under conditions of a shear index of 50 to 250 s$^{-1}$·K$^{-1}$ and a compression index of 0.5 to 5.5 mm$^{-1}$.

Hereinafter, the above preparation method will be described in detail for each step.

First, the step 1 is a step of preparing a hydrogel polymer, specifically, a step of performing thermal polymerization or photo-polymerization of a monomer composition comprising a water-soluble ethylene-based unsaturated monomer and a polymerization initiator in the presence of an internal crosslinking agent to form a hydrogel polymer.

The water-soluble ethylene-based unsaturated monomer contained in the monomer composition is the same as described above.

In addition, the monomer composition may include a polymerization initiator generally used in the production of a super absorbent polymer. As a non-limiting example, as the polymerization initiator, a thermal polymerization initiator, a photopolymerization initiator or the like may be used depending on the polymerization method. However, even in the case of the photo-polymerization method, a certain amount of heat is generated by ultraviolet irradiation or the like, and a certain amount of heat is generated in accordance with the progress of the polymerization reaction, which is an exothermic reaction, and thus, a thermal polymerization initiator may further be included.

The photo-polymerization initiator used herein may include, for example, one or more compounds selected from the group consisting of benzoin ether, dialkyl acetophenone, hydroxyl alkyl ketone, phenyl glyoxylate, benzyl dimethyl ketal, acyl phosphine and α-aminoketone. Among them, as a specific example of the acylphosphine, a commonly used lucyrin TPO, that is, 2,4,6-trimethyl-benzoyl-trimethyl phosphine oxide may be used. More various photo-polymerization initiators are well disclosed in "UV Coatings: Basics, Recent Developments and New Application" written by Reinhold Schwalm, (Elsevier, 2007), p 115, the content of which is incorporated herein by reference.

Moreover, as the thermal polymerization initiator, one or more compounds selected from the group consisting of a persulfate-based initiator, an azo-based initiator, hydrogen peroxide, and ascorbic acid may be used. Specific examples of the persulfate-based initiator may include sodium persulfate (Na$_2$S$_2$O$_8$), potassium persulfate (K$_2$S$_2$O$_8$), ammonium persulfate ((NH$_4$)$_2$S$_2$O$_8$), and the like. In addition, examples of the azo-based initiator may include 2,2-azobis(2-amidinopropane)dihydrochloride, 2,2-azobis-(N,N-dimethylene) isobutyramidine dihydrochloride, 2-(carbamoylazo)isobutylonitril, 2,2-azobis[2-(2-imidazolin-2-yl)propane] dihydrochloride, 4,4-azobis-(4-cyanovaleric acid) or the like. More various thermal polymerization initiators are well disclosed in "Principle of Polymerization" written by Odian, (Wiley, 1981), p 203, the content of which is incorporated herein by reference.

The polymerization initiator may be included in a concentration of about 0.001% to about 1% by weight based on the monomer composition. That is, when the concentration of the polymerization initiator is too low, the polymerization rate may become slow and a large amount of residual monomer may be extracted in the final product, which is not preferable. On the other hand, when the concentration of the polymerization initiator is too high, the polymer chains constituting the network become short, and thus the content of water-soluble components is increased and physical properties of the polymer may deteriorate such as a reduction in absorbency under pressure.

Meanwhile, the monomer composition may include a crosslinking agent ("internal crosslinking agent") to improve physical properties of the polymer by polymerization of the water-soluble ethylene-based unsaturated monomer. The crosslinking agent is used for internal crosslinking of the hydrogel polymer, and is used separately from a surface crosslinking agent described below.

As the internal crosslinking agent, any compound can be used as long as it enables introduction of cross-linked bond upon polymerization of the water-soluble ethylene-based unsaturated monomers. Non-limiting examples of the internal crosslinking agent may include multifunctional crosslinking agents, such as N,N'-methylenebisacrylamide, trimethylolpropane tri(meth)acrylate, ethylene glycol di(meth)acrylate, polyethylene glycol(meth)acrylate, propylene glycol di(meth)acrylate, polypropylene di(meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, pentaerythritol tetraacrylate, triallylamine, allyl(meth)acrylate, ethylene glycol diglycidyl ether, propylene glycol, glycerin, or ethylene carbonate, which may be used alone or in combination of two or more thereof, but are not limited thereto.

The internal crosslinking agent may be added at a concentration of about 0.001% by weight to 1% by weight, based on the monomer composition. That is, if the concentration of the internal crosslinking agent is too low, the absorption rate of the polymer lowers and the gel strength may become weak, which is undesirable. On the contrary, if the concentration of the internal crosslinking agent is too high, the absorption capacity of the polymer is lowered and thereby is not preferred for an absorbent.

In addition, the monomer composition may further include an additive such as a thickener, a plasticizer, a preservation stabilizer, an antioxidant, etc., if necessary.

Further, these monomer compositions can be prepared in the form of a solution in which raw materials such as the above-described monomers, polymerization initiator, internal crosslinking agent, etc. are dissolved in a solvent.

In this case, as the solvent, any solvent may be used without limitations in the constitution as long as it is able to dissolve the above raw materials. Examples of the solvent may include water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, or a mixture thereof.

The formation of the hydrogel polymer by polymerizing the monomer composition may be performed by a general polymerization method, and the process is not particularly limited. Non-limiting examples of the polymerization method are largely classified into the thermal polymerization and the photo-polymerization according to the polymerization energy source, and the thermal polymerization may be carried out in a reactor like a kneader equipped with agitating spindles arid the photo-polymerization may be carried out in a reactor equipped with a movable conveyor belt.

For example, the monomer composition is injected into a reactor like a kneader equipped with the agitating spindles, and thermal polymerization is performed by providing hot air thereto or heating the reactor, thereby obtaining the hydrogel polymer. In this case, the hydrogel polymer, which is discharged from the outlet of the reactor according to the type of agitating spindles equipped in the reactor, may be obtained as particles with a size of centimeters or millimeters. Specifically, the hydrogel polymer may be obtained in various forms according to the concentration of the monomer composition fed thereto, the feeding speed, or the like, and the hydrogel polymer having a (weight average) particle size of 2 mm to 50 mm may be generally obtained.

As another example, when the photo-polymerization of the monomer composition is performed in a reactor equipped with a movable conveyor belt, the hydrogel polymer may be obtained as a sheet. In this case, the thickness of the sheet may vary according to the concentration of the monomer composition fed thereto and the feeding speed, and the polymer sheet is preferably controlled to have a thickness of 0.5 cm to 10 cm in order to uniformly polymerize the entire sheet and secure production speed.

The hydrogel polymer formed by the above method may have a water content of about 40% by weight to 80% by weight. The "water content" as used herein means a weight occupied by moisture with respect to a total weight of the hydrogel polymer, which may be the value obtained by subtracting the weight of the dried polymer from the weight of the hydrogel polymer. Specifically, the water content can be defined as a value calculated by measuring the weight loss according to evaporation of water in the polymer during the drying process of increasing the temperature of the polymer with infrared heating. In this case, the drying conditions may be determined as follows: the drying temperature is increased from room temperature to about 180° C. and then the temperature may be maintained at 80° C., and the total drying time may be determined as 20 min, including 5 min for the temperature rising step.

The step 2 is a step of pulverizing the hydrogel polymer prepared in the step 1 above, wherein the hydrogel polymer is pulverized to reduce the size of the hydrogel polymer, thereby increasing the surface area and improving the efficiency of the drying described later. Furthermore, in the present invention, the shape and the like of the hydrogel polymer can be controlled by adjusting the pulverization condition, whereby the physical properties of the super absorbent polymer can be improved.

The pulverizing device used herein is not limited in its constitution, but specific examples thereof may include any one selected from the group consisting of a vertical pulverizer, a turbo cutter, a turbo grinder, a rotary cutter mill, a cutter mill, a disc mill, a shred crusher, a crusher, a chopper and a disc cutter. However, the present invention is not limited to the above-described example.

On the other hand, during the pulverization of the hydrogel polymer, a shear force and a compressive force is applied to the hydrogel polymer. The present invention comprises controlling the pulverization condition. Specifically, the pulverization of the hydrogel polymer is performed under conditions of a shear index of 50 to 250 $s^{-1} \cdot K^{-1}$ and a compression index of 0.5 to 5.5 $mm^1$.

The shear index is related to the force acting when pushing out the hydrogel polymer by a pulverizing device, and the compression index is related to the force acting when the hydrogel polymer passes through the pulverizing device. For example, when the hydrogel polymer is pulverized while pushing out the hydrogel polymer through a screw type extruder equipped inside a cylindrical pulverizer and passing the same through a perforated plate (chopper die) having holes, the compression index and the shear index can be calculated by the following Equations:

$$\text{Compression Index} = (L \times R^2)/(n \times r^4) \qquad [\text{Equation 3}]$$

in Equation 3,
L is the thickness (mm) of the perforated plate,
R is the radius (mm) of the perforated plate,
r is the radius (mm) of the hole of the perforated plate, and
n is the number of holes in the perforated plate, $$\text{Shear Index} = 2\omega Rc^2/(Rc^2 - Rs^2) \times (TSC/T) \qquad [\text{Equation 4}]$$

in Equation 4,
ω is 2×π×N/60 s, wherein N is the number of revolutions (rpm) of the screw,
Rc is the inner radius of the pulverizing device,
Rs is the radius of the screw,
TSC is the solid content (%) of the hydrogel polymer, and
T is the absolute temperature (K) of the hydrogel polymer.

According to the examples and comparative examples of the present invention, the super absorbent polymer of the example produced with the compression index and the shear index according to the present invention had the physical properties required in the present invention, whereas the super absorbent polymer of the comparative examples did not have the physical properties required in the present invention.

Further, when the hydrogel polymer is pulverized by the compression index and the shear index as described above, the surface area of the pulverized hydrogel polymer is remarkably increased. Specifically, in the pulverized hydrogel polymer, the percentage of the number of sheared particles is 0.35 or more and 0.95 or less. The "sheared particle" means a particle having three or more concave portions or holes with a depth of 10 μm or more observed on the pulverized hydrogel polymer particle, and the "number ratio of the sheared particles" means the number of the sheared particles relative to the total number of the hydrogel polymer particles. As described above, the sheared particles are produced and the surface area is widened, so that the physical properties of the super absorbent polymer can be improved.

On the other hand, the pulverization of the hydrogel polymer may be performed such that the hydrogel polymer has a particle diameter of 0.1 mm to 10 mm. That is, in order to increase the drying efficiency, the hydrogel polymer is preferably pulverized into particles with a size of 10 mm or less. However, since a phenomenon of agglomeration between particles may occur during excessive pulverization, the hydrogel polymer is preferably pulverized into particles with a size of 0.1 mm or more.

In addition, since pulverization of the hydrogel polymer is performed in a state of high water content, a phenomenon in which the hydrogel polymer adheres to the surface of the pulverizing device can occur. In order to minimize such a phenomenon, water, surfactant, agglomeration preventing agent (for example, clay, silica, etc.); persulfate-based initiators, azo-based initiators, hydrogen peroxide, thermal polymerization initiator, epoxy-based crosslinking agent, a diol crosslinking agent, a crosslinking agent containing difunctional, trifunctional or higher polyfunctional acrylate, crosslinking agent with mono-functionality containing a hydroxyl group or the like can be added to the hydrogel polymer as needed.

The step 3 is a step of drying the hydrogel polymer pulverized in the step 2.

The drying can be carried out at a temperature of 120 to 250° C., preferably 140 to 200° C., more preferably 150 to 190° C. In this case, the drying temperature can be defined as the temperature of the heating medium provided thereto for drying, or the internal temperature of the drying reactor including the heating medium and the polymer during the drying process. If the drying temperature is low, and therefore the drying time becomes long, the efficiency of the process may be deteriorated. In order to prevent this problem, the drying temperature is preferably 120° C. or higher. In addition, when the drying temperature is higher than necessary, the surface of the hydrogel polymer is excessively dried, and a fine powder may occur during the subsequent pulverization process and the physical properties of the polymer finally formed may be deteriorated. In order to prevent this problem, therefore, the drying temperature is preferably 250° C. or lower.

In this case, the drying time in the drying step is not particularly limited, but it may be controlled to 20 to 90 minutes at the above drying temperature, in consideration of the process efficiency.

The drying can be carried out using a conventional medium, and for example, the drying may be carried out by a method such as feeding hot air, irradiating infrared rays, irradiating microwaves, irradiating ultraviolet rays, or the like The drying is preferably carried out so that the dried polymer has a water content of about 0.1% to 10% by weight. That is, if the water content of the dried polymer is less than 0.1% by weight, production costs may be increased due to excessive drying and degradation of the crosslinked polymer may occur, which is not desirable. In addition, if the water content of the polymer is more than 10% by weight, defects may occur in a subsequent process, which is not desirable.

The step 4 is a step of pulverizing the polymer dried in the step 3, which is a step for optimizing the surface area. The pulverization can be carried out such that the pulverized polymer has a particle diameter of 150 to 850 μm.

Examples of the pulverizing device that can be used herein include a pin mill, a hammer mill, a screw mill, a roll mill, a disc mill, a jog mill or the like.

Further, in order to control the physical properties of the super absorbent polymer finally produced, the step of selectively classifying particles having a particle diameter of 150 to 850 μm in the polymer particles obtained through the above-mentioned pulverization step may be further performed.

On the other hand, through the classification, polymer particles having a particle diameter of less than 150 μm can be assembled with a solvent (for example, water) usable in the step 1 to prepare a reassembled body of a fine powder. The fine powder-reassembled body may be added to the super absorbent polymer of the step 2 described above. Specifically, the addition of the fine powder-reassembled body may be performed immediately before pulverization, during pulverization, or after pulverization in the step 2. In addition, the addition amount of the fine powder-reassembled body is preferably 30% by weight or less based on the hydrogel polymer of the step 2 above.

Step 5 is a step of surface-modifying the polymer pulverized in the step 4.

The surface modification induces a crosslinking reaction on the surface of the pulverized polymer in the presence of a second crosslinking agent (surface crosslinking agent). Through such surface modification, a surface modified layer (surface crosslinked layer) is formed on the surface of the pulverized polymer particles.

The surface modification may be performed by a conventional method for increasing the cross-linking density of the surface of the polymer particles. For example, it may be performed by a method of mixing a solution containing a second crosslinking agent (surface crosslinking agent) with the pulverized polymer followed by a crosslinking reaction.

Herein, the second crosslinking agent is a compound capable of reacting with a functional group of the polymer, and is preferably an alkylene carbonate having 2 to 5 carbon atoms. More preferably, ethylene carbonate can be used as the second crosslinking agent. In addition to the second crosslinking agent, it may further include porous silica, clay and the like. Further, in order to control the penetration rate and depth of the second crosslinking agent, an acidic compound, a polymer, or the like can be further added, if necessary.

At this time, the content of the second crosslinking agent may be appropriately controlled according to the kind of crosslinking agent, reaction conditions, etc., and may be preferably adjusted to 0.001 to 5 parts by weight based on 100 parts by weight of the pulverized polymer. If the content of the second crosslinking agent is too low, the surface modification may not be properly performed, and the physical properties of the final resin may be deteriorated. Conversely, if an excess amount of the second crosslinking agent is used, the absorption capacity of the polymer may rather decrease due to excessive surface crosslinking reaction, which is not preferable.

On the other hand, the surface modification step may be performed by a method in which the second crosslinking agent and the pulverized polymer are added to a reaction vessel and mixed, a method in which the second crosslinking agent is injected into the pulverized polymer, a method in which the pulverized polymer and the second crosslinking agent are continuously supplied and mixed, and the like.

Moreover, when adding the second crosslinking agent, water may be further added. Thus, adding the second crosslinking agent and water together may induce uniform dispersion of the second crosslinking agent, prevent the aggregation phenomenon of the polymer particles, and further optimize the penetration depth of the second crosslinking agent to the polymer particles. In consideration of these objects and effects, the content of water to be added together with the second crosslinking agent may be adjusted to 0.5 to 10 parts by weight based on 100 parts by weight of the pulverized polymer.

The surface modification step may be proceeded at a temperature of 100 to 250° C. Further, the surface modification can be proceeded for 1 minute to 120 minutes, preferably 1 minute to 100 minutes, more preferably 10 minutes to 80 minutes. That is, in order to prevent the polymer particles from being damaged to thereby decrease their physical properties during excessive reaction while inducing the minimum surface cross-linking reaction, the surface modification step may be carried out under the above-mentioned conditions.

Advantageous Effects

The super absorbent polymer according to the present invention is excellent in various physical properties required for a super absorbent polymer, while exhibiting excellent water absorption capacity, absorption rate and liquid permeability. Therefore, the super absorbent polymer according to the present invention can be usefully used as a sanitary material such as a diaper, particularly an ultrathin sanitary material.

BRIEF DESCRIPTION OF DRAWINGS

FIG. 1 shows an SEM image of the sheared particles (FIG. 1(a)) and the non-sheared particles (FIG. 1(b)) in the pulverized hydrogel polymer produced according to the present invention.

DETAILED DESCRIPTION OF THE EMBODIMENTS

Hereinafter, preferred examples are presented to aid in understanding of the invention. However, the following examples are provided only to illustrate the present invention, and the scope of the present invention is not limited thereto.

EXAMPLE AND COMPARATIVE EXAMPLE

As the manufacturing apparatus of a super absorbent polymer, a continuous manufacturing apparatus comprising a polymerization step, a hydrogel pulverizing step, a drying step, a pulverization step, a classification step, a surface cross-linking step, a cooling step, a classification step, and a transport step connecting respective steps can be used.

(Step 1)

0.4 parts by weight of polyethylene glycol diacrylate (weight average molecular weight: ~500 g/mol) as an internal cross-linking agent, 0.1 part by weight of hexanediol diacrylate and 0.01 part by weight of IRGACURE 819 as a photoinitiator were mixed in 100 parts by weight of acrylic acid to prepare a monomer solution. Subsequently, while continuously supplying the monomer solution by a metering pump, 160 parts by weight of a 24 wt % aqueous solution of sodium hydroxide was continuously subjected to line mixing to prepare an aqueous monomer solution. At this time, the temperature raised by the neutralizing heat was adjusted to 40° C. Further, 6 parts by weight of a 4 wt % aqueous solution of sodium persulfate was continuously subjected to line mixing, and then continuously supplied to a continuous polymerization reactor having a planar polymerization belt with a dam at each end. Thereafter, UV light was irradiated for 1 minute, and further thermal polymerization was carried out for 2 minutes to prepare a hydrogel.

(Step 2)

The hydrogel prepared in the step 1 was cut to have an average size of about 300 mm or less, and then introduced into a pulverizer together with a reassembled body of fine powder as shown in Table 1 below and pulverized under the respective conditions. Herein, the fine powder-reassembled body used the fine powder-reassembled body prepared in step 4 below, and the input ratio is shown in Table 1 as weight % relative to the hydrogel.

TABLE 1

| | N | Rc | Rs | TSC | T | Shear index | L | r | n | R | Compression index | Input ratio of fine powder-reassembled body |
|---|---|---|---|---|---|---|---|---|---|---|---|---|
| Unit | rpm | mm | mm | % | K | $s^{-1}K^{-1}$ | mm | mm | — | mm | $mm^{-1}$ | Wt % |
| Ex. 1 | 160 | 102 | 100 | 53 | 350 | 130.7 | 30 | 6 | 250 | 130 | 1.56 | 18 |
| Ex. 2 | 185 | 102 | 100 | 53 | 350 | 151.1 | 30 | 6 | 250 | 130 | 1.56 | 18 |
| Ex. 3 | 185 | 102 | 100 | 55 | 350 | 156.8 | 35 | 6 | 250 | 130 | 1.83 | 18 |
| Ex. 4 | 185 | 102 | 100 | 53 | 330 | 160.3 | 35 | 6 | 200 | 130 | 2.28 | 18 |
| Ex. 5 | 185 | 102 | 100 | 53 | 350 | 151.1 | 35 | 5 | 350 | 130 | 2.70 | 18 |

TABLE 1-continued

|  | N | Rc | Rs | TSC | T | Shear index | L | r | n | R | Compression index | Input ratio of fine powder-reassembled body |
|---|---|---|---|---|---|---|---|---|---|---|---|---|
| Unit | rpm | mm | mm | % | K | $s^{-1}K^{-1}$ | mm | mm | — | mm | $mm^{-1}$ | Wt % |
| Ex. 6 | 185 | 102 | 100 | 53 | 330 | 160.3 | 40 | 4 | 560 | 130 | 4.72 | 25 |
| Comp. Ex. 1 | 80 | 102 | 100 | 40 | 365 | 47.3 | 25 | 10 | 100 | 130 | 0.42 | 18 |
| Comp. Ex. 2 | 160 | 102 | 101 | 53 | 350 | 260.1 | 40 | 4 | 460 | 130 | 5.74 | 18 |
| Comp. Ex. 3 | 160 | 102 | 101 | 53 | 350 | 260.1 | 25 | 10 | 100 | 130 | 0.42 | 18 |

In Table 1, the shear index and the compression index each were calculated as follows.

$$\text{Shear Index} = 2\omega Rc^2/(Rc^2-Rs^2) \times (TSC/T), \omega = 2 \times \pi \times N/60 \, s$$

$$\text{Compression Index} = (L \times R^2)/(n \times r^4)$$

The definitions of the respective variables used in the calculation of the shear index and the compression index are the same as those defined in the specification.

(Step 3)

Subsequently, the hydrogel pulverized in the step 2 was dried in a drier capable of moving the air volume up and down. The hydrogel was uniformly dried by allowing hot air of 180° C. to flow upward from downward to the top for 15 minutes so that the water content of the dried powder was about 2% or less, and again allowing the hot air to flow downward from upward for 15 minutes.

(Step 4)

The resin dried in step 3 was pulverized by a pulverizing device and then classified to obtain a base polymer having a size of 150 to 850 μm. On the other hand, the polymer particles having a particle diameter of less than 150 μm through the above classification were assembled with water and used as the fine powder-reassembled body of step 2 described above.

(Step 5)

Then, 100 parts by weight of the base polymer prepared in the step 4 was mixed with a crosslinking agent solution in which 3 parts by weight of water, 3 parts by weight of methanol and 0.5 part by weight of ethylene carbonate were mixed, and then the mixture was subjected to surface crosslinking reaction at 180° C. for 40 minutes. Next, the obtained product was cooled and then classified to obtain a surface-crosslinked super absorbent polymer having a particle diameter of 150 to 850 μm.

EXPERIMENTAL EXAMPLE

The physical properties of the respective super absorbent polymers prepared in Examples and Comparative Examples were measured and evaluated by the following methods.

(1) Centrifuge Retention Capacity (CRC)

The centrifuge retention capacity (CRC) by water absorption capacity under a non-loading condition was measured in accordance with EDANA (European Disposables and Nonwovens Association) recommended test method No. WSP 241.3.

After uniformly inserting $W_0(g)$ (about 0.2 g) of the super absorbent polymers in a nonwoven fabric-made bag and sealing the same, it was soaked in a physiological saline solution composed of 0.9 wt % aqueous sodium chloride solution at room temperature. After 30 minutes, the bag was dehydrated by using a centrifuge at 250 G for 3 minutes, and then the weight $W_2(g)$ of the bag was measured. Further, after carrying out the same operation without using the super absorbent polymer, the weight $W_1(g)$ of the bag was measured. CRC (g/g) was calculated by using the obtained weight values according to the following Equation 1, thereby confirming the centrifuge retention capacity.

$$CRC(g/g) = \{[W_2(g) - W_1(g) - W_0(g)]/W_0(g)\} \quad \text{[Equation 1]}$$

(2) Absorbency Under Pressure (AUP)

The absorbency under pressure was measured in accordance with EDANA (European Disposables and Nonwovens Association) recommended test method No. WSP 242.3.

First, a 400 mesh stainless steel net was installed in the cylindrical bottom of a plastic having an internal diameter of 60 mm. $W_0(g, 0.90 g)$ of the super absorbent polymers were uniformly scattered on the steel net under conditions of temperature of 23±2° C. and relative humidity of 45%, and a piston which can provide a load of 4.83 kPa (0.7 psi) uniformly was put thereon. The external diameter of the piston was slightly smaller than 60 mm, there was no gap between the cylindrical internal wall and the piston, and the jig-jog of the cylinder was not interrupted. At this time, the weight $W_3(g)$ of the device was measured. After putting a glass filter having a diameter of 125 mm and a thickness of 5 mm in a Petri dish having a diameter of 150 mm, a physiological saline solution composed of 0.90 wt % of sodium chloride was poured in the dish until the surface level became equal to the upper surface of the glass filter. A sheet of filter paper having a diameter of 120 mm was put thereon. The measuring device was put on the filter paper and the solution was absorbed under a load for about 1 hour. After 1 hour, the weight $W_4(g)$ was measured after lifting the measuring device up. Using the respective mass fractions thus obtained, AUP(g/g) was calculated according to the following Equation 2, thereby confirming the absorbency under pressure.

$$AUP(g/g) = [W_4(g) - W_3(g)]/W_0(g) \quad \text{[Equation 2]}$$

(3) Saline Flow Conductivity (SFC)

The physiological saline flow induction (SFC) was measured and calculated according to the methods disclosed in columns 54 to 59 of U.S. Pat. No. 5,562,646.

(4) T-20

9 g of sodium chloride and 0.1 g of Lorodac (main component: linear alcohol ethoxylate having 12 to 14 carbon atoms, CAS #68439-50-9) were dissolved in 1 L of distilled water to make a aqueous solution, and the T-20 was calculated and measured with the time required for absorbing 1 g of the superabsorbent resin to 20 g of this aqueous solution. Specific measurement methods of T-20 were described in detail on pages 13 to 18 of European Patent Publication No. 2,535,027.

(5) FSR (Free Swell Rate)

The FSR of the base polymer powder or the super absorbent polymer was measured and calculated by using those classified into #30 to #50 (for example, those having a particle diameter of 300 to 600 μm) according to the method disclosed on pages 22 to 23 of European Patent Publication No. 2535027.

(6) Number of Sheared Particle

It was calculated by observing the super absorbent polymer particles with a scanning electron microscope (SEM) and dividing the number of sheared particles as defined therein into the total number of particles. As an example of the sheared particles, the results of observation of the super absorbent polymer of Example 1 are shown in FIG. 1, wherein FIG. 1(*a*) shows the sheared particles and FIG. 1(*b*) shows the particles not corresponding thereto.

The results are shown in Table 2 below.

TABLE 2

| | CRC | AUP | FSR | SFC | T-20 | Number ratio of sheared particles |
|---|---|---|---|---|---|---|
| Unit | g/g | g/g | g/g/s | $10^{-7} cm^3 \cdot s/g$ | s | — |
| Example 1 | 26.7 | 24.4 | 0.28 | 96 | 159 | 0.41 |
| Example 2 | 26.5 | 24.2 | 0.28 | 95 | 156 | 0.44 |
| Example 3 | 26.3 | 24.0 | 0.29 | 96 | 154 | 0.49 |
| Example 4 | 26.2 | 23.9 | 0.30 | 91 | 147 | 0.57 |
| Example 5 | 26.1 | 23.9 | 0.30 | 87 | 143 | 0.61 |
| Example 6 | 25.5 | 22.3 | 0.35 | 78 | 125 | 0.83 |
| Comparative Example 1 | 26.6 | 24.5 | 0.11 | 53 | 293 | 0.02 |
| Comparative Example 2 | 23.3 | 20.2 | 0.42 | 18 | 104 | 0.99 |
| Comparative Example 3 | 24.5 | 20.7 | 0.37 | 25 | 121 | 0.96 |

The invention claimed is:

1. A super absorbent polymer comprising:
    a base layer comprising a first crosslinked polymer; and
    a surface-crosslinked layer disposed on the base layer, the surface-crosslinked layer comprising a second crosslinked polymer,
    wherein the first crosslinked polymer is prepared from a water-soluble ethylene-based unsaturated monomer having an acidic group, wherein at least a part of the acidic group is neutralized, and
    wherein the second crosslinked polymer is prepared by crosslinking the first crosslinked polymer using a surface crosslinking agent,
    wherein the super absorbent polymer has:
    a centrifuge retention capacity (CRC) for a physiological saline solution (0.9 wt % aqueous sodium chloride solution) for 30 minutes, of 25 g/g or more,
    an absorbency under pressure (AUP) for a physiological saline solution (0.9 wt % aqueous sodium chloride solution) under 0.7 psi for 1 hour, of 21 g/g or more,
    a saline flow conductivity (SFC) for a physiological saline solution (0.685 wt % aqueous sodium chloride solution), of $30(\cdot 10^{-7} cm^3 \cdot s/g)$ or more, and
    T-20 indicating the time required for absorbing 1 g of the super absorbent polymer to 20 g of 0.9 wt % sodium chloride and 0.01 wt % aqueous solution of alcohol ethoxylate having 12 to 14 carbon atoms, of 190 seconds or less, and
    a free swell rate (FSR) of 0.20 g/g/s or more, when 1 g of the super absorbent polymer absorbs 20 g of a 0.9 wt % aqueous sodium chloride solution.

2. The super absorbent polymer according to claim 1, wherein the water-soluble ethylene-based unsaturated monomer includes at least one selected from the group consisting of an anionic monomer such as acrylic acid, methacrylic acid, maleic anhydride, fumaric acid, crotonic acid, itaconic acid, 2-acryloyl ethane sulfonic acid, 2-(meth) acryloylethanesulfonic acid, or 2-(meth)acrylamide-2-methyl propane sulfonic acid, and a salt thereof; a nonionic hydrophilic monomer such as (meth)acrylamide, N-substituted (meth)acrylate, 2-hydroxyethyl(meth)acrylate, 2-hydroxypropyl(meth)acrylate, methoxypolyethyleneglycol (meth) acrylate, or polyethyleneglycol(meth)acrylate; and an unsaturated monomer containing amino group such as (N,N)-dimethylaminoethyl(meth)acrylate or (N,N)-dimethylaminopropyl(meth) acrylamide, and a quaternary compound thereof.

3. The super absorbent polymer according to claim 1, wherein the first crosslinked polymer includes a polymer in which the monomer is crosslinked in the presence of at least one internal crosslinking agent selected from the group consisting of N,N'-methylenebisacrylamide, trimethylol propane tri(meth)acrylate, ethylene glycol di(meth)acrylate, polyethylene glycol di(meth)acrylate, propylene glycol di(meth)acrylate, polyproplyene glycol di(meth)acrylate, butane diol di(meth)acrylate, butylene glycol di(meth)acrylate, diethylene glycol di(meth)acrylate, hexane diol di(meth)acrylate, triethylene glycol di(meth)acrylate, tripropylene glycol di(meth) acrylate, tetraethylene glycol di(meth)acrylate, dipentaerythritol pentaacrylate, glycerin tri(meth)acrylate, pentaerythritol tetraacrylate, allyl(meth)acrylate, ethylene glycol diglycidyl ether, propylene glycol, glycerin, or ethylene carbonate.

4. The super absorbent polymer according to claim 1, wherein the base layer has a particle diameter of 150 to 850 μm.

* * * * *